(12) United States Patent
Yamato (10) Patent No.: US 11,351,768 B2
(45) Date of Patent: Jun. 7, 2022

(54) SHAPED SHEET MANUFACTURING METHOD

(71) Applicant: ZUIKO CORPORATION, Settu (JP)

(72) Inventor: Shigeaki Yamato, Settu (JP)

(73) Assignee: ZUIKO CORPORATION, Settu (JP)

( * ) Notice: Subject to any disclaimer, the term of this patent is extended or adjusted under 35 U.S.C. 154(b) by 0 days.

(21) Appl. No.: 17/281,151

(22) PCT Filed: Oct. 24, 2019

(86) PCT No.: PCT/JP2019/041790
§ 371 (c)(1),
(2) Date: Mar. 29, 2021

(87) PCT Pub. No.: WO2020/085460
PCT Pub. Date: Apr. 30, 2020

(65) Prior Publication Data
US 2021/0339521 A1 Nov. 4, 2021

(30) Foreign Application Priority Data
Oct. 24, 2018 (JP) .............................. JP2018-200202

(51) Int. Cl.
*B32B 38/06* (2006.01)
*B32B 5/26* (2006.01)
(Continued)

(52) U.S. Cl.
CPC .............. *B32B 38/06* (2013.01); *B32B 5/022* (2013.01); *B32B 5/266* (2021.05); *B32B 37/10* (2013.01);
(Continued)

(58) Field of Classification Search
CPC . B32B 38/06; B32B 2309/16; B32B 38/1875; Y10T 156/1023; A61F 13/15731; B31F 1/07
See application file for complete search history.

(56) References Cited

U.S. PATENT DOCUMENTS 5,763,333 A * 6/1998 Suzuki ................... B32B 5/022
442/351
5,882,769 A 3/1999 McCormack et al.
(Continued)

FOREIGN PATENT DOCUMENTS

| JP | H06-255006 A | 9/1994 |
|---|---|---|
| JP | 4090420 B2 | 5/2008 |

(Continued)

OTHER PUBLICATIONS

PCT/ISA/210, "International Search Report for International Application No. PCT/JP2019/041790," dated Jan. 21, 2020.

*Primary Examiner* — Carson Gross
(74) *Attorney, Agent, or Firm* — Manabu Kanesaka (57) ABSTRACT

In a shaped sheet manufacturing method, it is possible to reliably shape a first sheet even if the tension of the first sheet is reduced at the time of manufacturing the shaped sheet. In a first step, a first sheet is conveyed along an outer peripheral surface of a first roll having a plurality of recessed parts. In a second step, a second sheet is overlapped with the first sheet and conveyed together with the first sheet so that the first and second sheets are held between the recessed parts of the first roll and projection parts of a second roll. In a third step, the first and second sheets having passed between the first roll and the second roll are bonded to each other. In the second step, the tension of the first sheet is made smaller than the tension of the second sheet.

9 Claims, 10 Drawing Sheets

(51) Int. Cl.
*B32B 5/02* (2006.01)
*B32B 37/10* (2006.01)
*A61F 13/15* (2006.01)

(52) U.S. Cl.
CPC ..... *A61F 13/15731* (2013.01); *B32B 2555/02* (2013.01); *Y10T 156/1023* (2015.01)

(56) References Cited

U.S. PATENT DOCUMENTS

| | | |
|---|---|---|
| 2002/0023708 A1* | 2/2002 | Tronchetti ........ A61F 13/15731 156/212 |
| 2004/0140047 A1 | 7/2004 | Sato et al. |
| 2005/0069679 A1* | 3/2005 | Stelljes .................... B32B 7/12 428/156 |
| 2009/0092797 A1 | 4/2009 | Sato et al. |
| 2010/0209664 A1 | 8/2010 | Sato et al. |
| 2011/0042011 A1 | 2/2011 | Sato et al. |
| 2015/0290050 A1 | 10/2015 | Wada |
| 2016/0263271 A1* | 9/2016 | Huang .................... A61L 15/60 |
| 2017/0066219 A1* | 3/2017 | Bonelli ............. A61F 13/15699 |
| 2018/0140478 A1 | 5/2018 | Fukuhara |

FOREIGN PATENT DOCUMENTS

| | | |
|---|---|---|
| JP | 2009-126107 A | 6/2009 |
| JP | 2016-87423 A | 5/2016 |
| WO | 2014/084066 A1 | 6/2014 |
| WO | 2016/199543 A1 | 12/2016 |

* cited by examiner

--Prior Art--

Fig. 11 --Prior Art--

SHAPED SHEET MANUFACTURING METHOD

RELATED APPLICATIONS

The present application is National Phase of International Application No. PCT/JP2019/041790 filed Oct. 24, 2019, and claim priority from Japanese Application No. 2018-200202, filed Oct. 24, 2018, the disclosures of which are hereby incorporated by reference herein in its entirety.

TECHNICAL FIELD

The present invention relates to a shaped sheet manufacturing method, and more specifically, relates to a technique of manufacturing a shaped sheet in which protruding parts are formed on at least one of two sheets bonded to each other.

BACKGROUND ART

Figure 10:
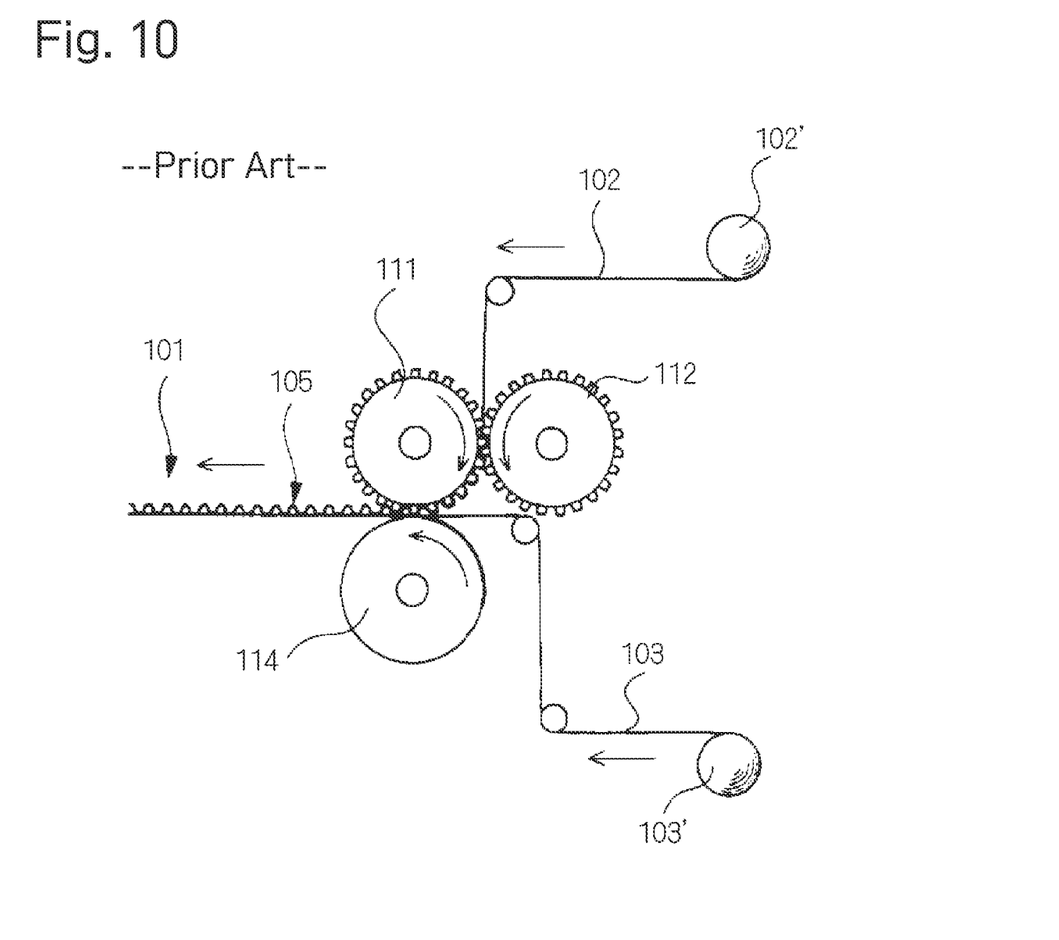
FIG. 10 is an explanatory view of the shaped sheet manufacturing method (first conventional example).

A shaped sheet in which protruding parts are formed on at least one of two sheets bonded to each other is used for, for example, disposable wearable articles such as paper diapers so that the protruding parts are in contact with the skin. The shaped sheet like this is manufactured as follows:

FIG. 10 is an explanatory view of a method of manufacturing a shaped sheet 101. As shown in FIG. 10, a first sheet 102 sent from a web roll 102' is held between a pair of shaping rolls 111 and 112 where projections and depressions that engage with each other are formed on the outer peripheral surfaces thereof, and the first sheet 102 is shaped. Then, a second sheet 103 sent from a web roll 103' is overlapped with the first sheet 102 biting the projections and depressions on the outer peripheral surface of the one shaping roll 111, and the sheets 102 and 103 are both held between the one shaping roll 111 and an anvil roll 114 and heated, thereby bonding the sheets 102 and 103 to each other. In this way, the shaped sheet 101 where protruding parts 105 are formed on the first sheet 102 is manufactured (for example, see Patent Literature 1).

Figure 11:
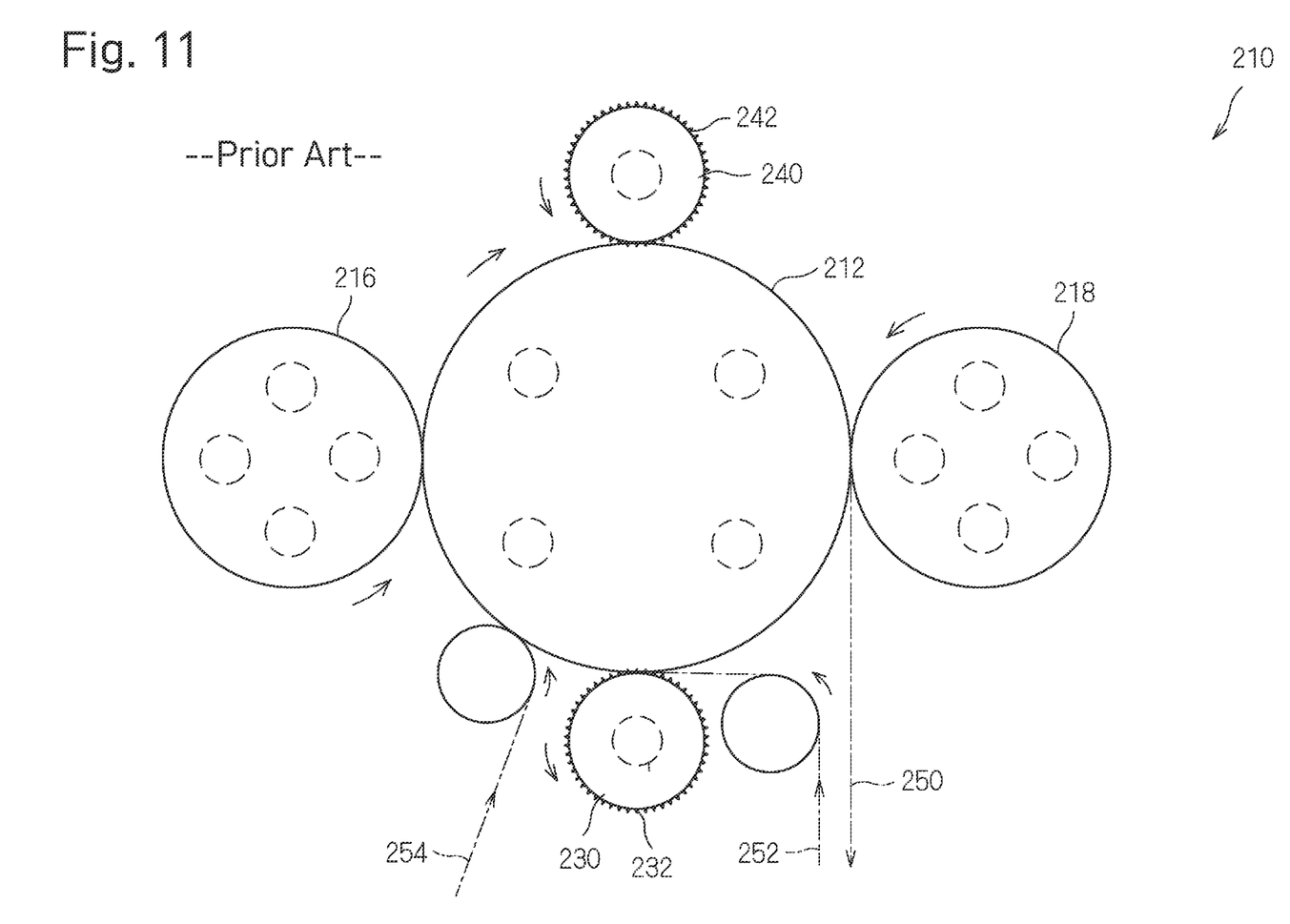
FIG. 11 is an explanatory view of the shaped sheet manufacturing method (second conventional example).

FIG. 11 is an explanatory view of a method of manufacturing another shaped sheet 250. As shown in FIG. 11, a shaped sheet manufacturing device 210 is used in which a first and second shaping rolls 230 and 240 having a plurality of projection parts 232 and 242 on the outer peripheral surfaces thereof and a first and second bonding rolls 216 and 218 are disposed around a main roll 212 where a plurality of non-illustrated recessed parts are formed on the outer peripheral surface thereof. First, a first sheet 252 is conveyed along the outer periphery of the main roll 212, and the first sheet 252 is pressed into the recessed parts of the main roll 212 by the projection parts 232 of the first shaping roll 230, thereby shaping the first sheet 252. Then, a second sheet 254 is overlapped with the first sheet 252, held between the main roll 212 and the first bonding roll 216 and heated, thereby bonding the sheets 252 and 254 to each other. Then, the second sheet 254 is pressed into the recessed parts of the main roll 212 by the projection parts 242 of the second shaping roll 240, thereby shaping the second sheet 254. Then, the sheets 252 and 254 are held between the main roll 212 and the second bonding roll 218 and heated, thereby reinforcing the bonding of the sheets 252 and 254 (for example, see Patent Literature 2).

PRIOR ART LITERATURES

Patent Literatures

[Patent Literature 1] Japanese Patent No. 4090420
[Patent Literature 2] WO 2016/199543

SUMMARY OF THE INVENTION

Problem to be Solved by the Invention

In a case where shaping is performed with the projections and depressions engaging with each other as in Patent Literature 1, the tension of the first sheet 102 is reduced. However, when the tension of the first sheet 102 is reduced, there are cases where the parts of the first sheet 102 pressed into the recessed parts of the one shaping roll 111 are caught by the projection parts of the other shaping roll 112 and disengaged from the recessed parts. The disengagement of the first sheet 102 from the recessed parts causes a problem in that it is impossible to bond the first and second sheets 102 and 103 at predetermined places.

When both the first and second sheets 252 and 254 are shaped as in Patent Literature 2, the second shaping roll 240 that shapes the second sheet 254 is necessary separately from the first shaping roll 230 that shapes the first sheet 252, which makes the device configuration complex.

In view of such circumstances, a problem to be solved by the present invention is to provide a shaped sheet manufacturing method with which it is possible to reliably shape the first sheet even if the tension of the first sheet is reduced at the time of manufacturing the shaped sheet in which the first and second sheets are bonded to each other and with which it is possible to shape both the first and second sheets without making the device configuration complex.

Means for Solving the Problem

To solve the above-mentioned problem, the present invention provides a shaped sheet manufacturing method configured as follows:

A shaped sheet manufacturing method uses a shaped sheet manufacturing device that is provided with a first roll having a plurality of recessed parts on an outer peripheral surface thereof and a second roll having a plurality of projection parts on an outer peripheral surface thereof and in which the first and second rolls are disposed adjacent to each other and rotate in synchronism and the recessed parts and the projection parts engage with each other with space therebetween. The shaped sheet manufacturing method is provided with: (i) a first step of conveying a first sheet which is a continuous body along the outer peripheral surface of the first roll which is rotating; (ii) a second step of overlapping a second sheet which is a continuous body with the first sheet and conveying the second sheet together with the first sheet so that the first sheet and the second sheet pass between the first roll and the second roll and are held between the recessed parts and the projection parts; and (iii) a third step of bonding to each other the first and second sheets having passed between the first roll and the second roll. In the second step, the tension of the first sheet is made smaller than the tension of the second sheet.

According to the above-described method, since the parts of the first sheet pressed into the recessed parts are covered with the second sheet and are not in contact with the projection parts, even if the tension of the first sheet is made smaller than the tension of the second sheet, the parts of the first sheet pressed into the recessed parts are never caught by the projection parts and disengaged from the recessed parts. Consequently, even if the tension of the first sheet is reduced, the first sheet can be reliably shaped.

The second sheet is shaped in a case where parts or the whole of the parts pressed into the recessed parts by the projection parts remain in the recessed parts when it passes between the first roll and the second roll. In this case, although both the first and second sheets can be simultaneously shaped, it is unnecessary to prepare a roll the shapes the second sheet, separately from the roll that shapes the first sheet. Consequently, it is possible to shape both the first and second sheets without making the configuration of the shaped sheet manufacturing device complex.

Preferably, in the third step, the first and second sheets are bonded to each other by using a bonder disposed adjacent to the first roll under a condition where parts of the first sheet pressed into the recessed parts by the projection parts remain in the recessed parts.

In this case, the first sheet can be reliably bonded to the second sheet at predetermined places around the parts pressed into the recessed parts by the projection parts, so that the shape of the shaped sheet is stabilized.

Preferably, in the second step, the second sheet is overlapped with the first sheet so that the second sheet starts to overlap with the first sheet in an area where the recessed parts and the projection parts engage with each other with space therebetween.

In this case, since the first and second sheets are not in contact with each other on the upstream side in the conveyance direction of the area where the recessed parts and the projection parts engage with each other with space therebetween, it is easy to adjust the tensions of the first and second sheets independently of each other.

Preferably, the first and second sheets are non-stretchable non-woven sheets.

In this case, a shaped sheet suitable for disposable wearable articles can be manufactured.

Effects of the Invention

According to the present invention, even if the tension of the first sheet is reduced at the time of manufacturing the shaped sheet in which the first and second sheets are bonded to each other, it is possible to reliably shape the first and second sheets, and it is possible to shape both the first and second sheets without making the device configuration complex.

MODE FOR CARRYING OUT THE INVENTION

Hereinafter, an embodiment of the present invention will be described with reference to the drawings.

<First embodiment> A shaped sheet manufacturing method of the first embodiment will be described with reference to FIGS. 1 to 9.

Figure 1:
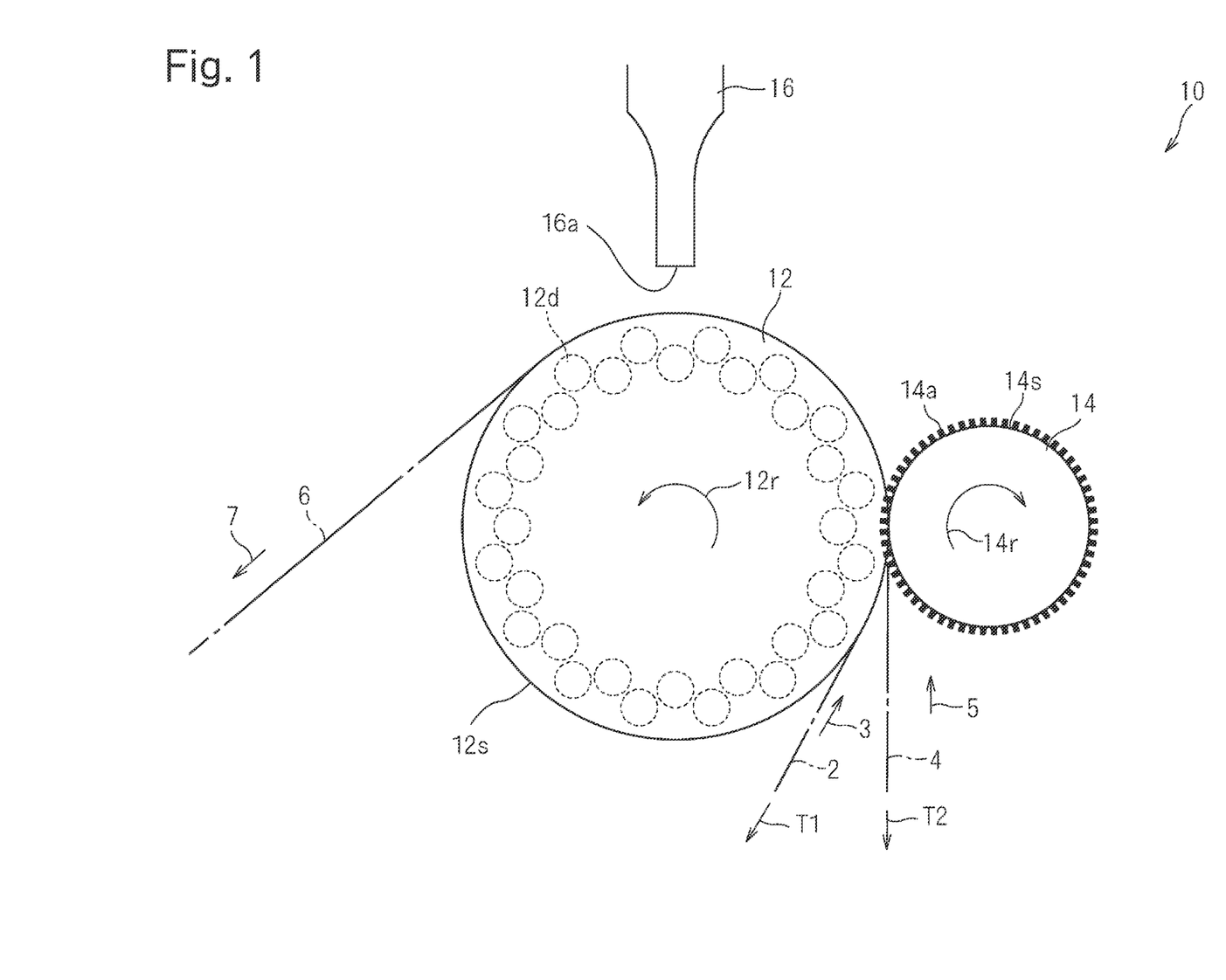
FIG. 1 is a schematic diagram of a shaped sheet manufacturing device (first embodiment).
Figure 2:
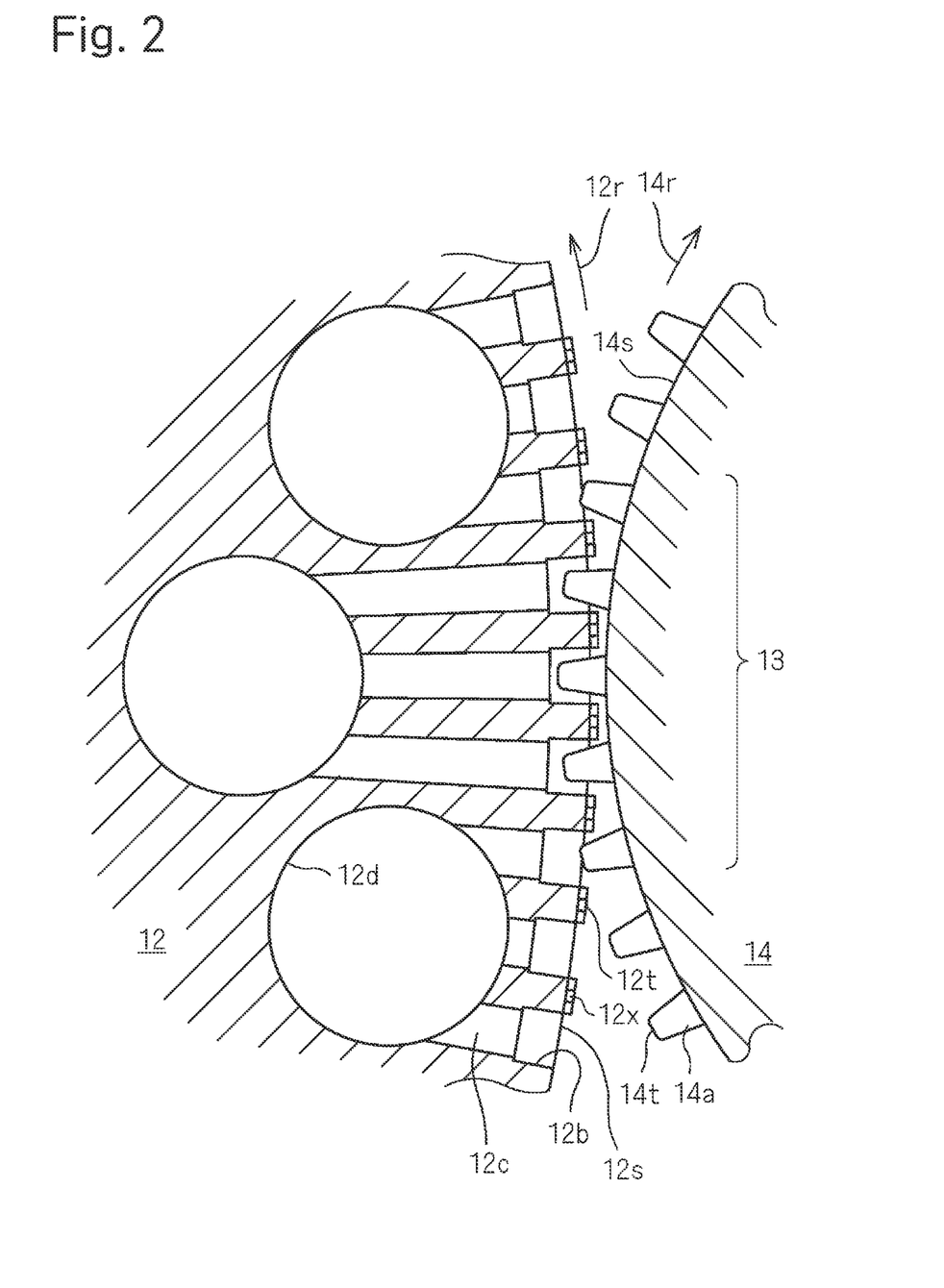
FIG. 2 is an enlarged cross-sectional view of a relevant part of the shaped sheet manufacturing device (first embodiment).

FIG. 1 is a schematic diagram of a shaped sheet manufacturing device 10 used for the shaped sheet manufacturing method of the first embodiment. FIG. 2 is an enlarged cross-sectional view of a relevant part of the shaped sheet manufacturing device 10. As shown in FIGS. 1 and 2, the shaped sheet manufacturing device 10 is provided with a first and second rolls 12 and 14 disposed adjacent to each other and a bonder 16 disposed adjacent to the first roll 12.

The first roll 12 has, on a cylindrical outer peripheral surface $12s$, a plurality of recessed parts $12b$ retracted inward in a radial direction from the outer peripheral surface $12s$ (see FIG. 2). The second roll 14 has, on a cylindrical outer peripheral surface $14s$, a plurality of projection parts $14a$ projecting outward in a radial direction from the outer peripheral surface $14s$. The first and second rolls 12 and 14 rotate in synchronism in directions opposite to each other as indicated by the arrows $12r$ and $14r$, and as shown in FIG. 2, the recessed parts $12b$ of the first roll 12 and the projection parts $14a$ of the second roll 14 are configured so as to engage with each other with space therebetween, that is, without being in contact with each other in an engagement area 13. It is preferable that the recessed parts $12b$ and the projection parts $14a$ be two-dimensionally arranged at intervals therebetween on the outer peripheral surfaces $12s$ and $14s$ of the first and second rolls 12 and 14 so as to simultaneously engage with each other at a plurality of places.

As shown in FIG. 1, a first sheet 2 which is a continuous body is wound around the outer peripheral surface $12s$ of the first roll 12, further, a second sheet 4 which is a continuous body is wound on the first sheet 2, and the first and second sheets 2 and 4 are conveyed in the directions indicated by the arrows 3 and 5 with the rotation of the first roll 12. Although detailed later, when the first and second sheets 2 and 4 pass between the first roll 12 and the second roll 14, at least the first sheet 2 is shaped, and then, when passing between the first roll 12 and the bonder 16, the first and second sheets 4 are bonded to each other. A finished shaped sheet 6 is separated from the first roll 12 as indicated by the arrow 7, conveyed to the post-process, and used for, for example, disposable wearable articles such as paper diapers.

At least the insides of the recessed parts $12b$ of the first roll 12 may be heated, whereby shaping is more reliably performed. For example, a heater is provided inside the first roll 12 and the periphery of the recessed parts $12b$ is heated. The heating may be performed on both the first and second rolls 12 and 14.

As shown in FIG. 2, in the first roll 12, suction flow passages $12c$ and $12d$ communicating with the bottoms of the recessed parts $12b$ and seal projections $12x$ projecting outward in a radial direction from the outer peripheral surface $12s$ are formed. The recessed parts $12b$ of the first roll 12 are connected to a negative pressure source through the suction flow passages 12c and 12d. Thereby, the first sheet 2 disposed along the outer peripheral surface 12s of the first roll 12 is sucked and held. The suction flow passages 12c and 12d and the seal projections 12x may be eliminated.

The projection parts 14a of the second roll 14 are formed in the shape of, for example, a truncated pyramid where ends 14t are flat. The shape of the projection parts 14a of the second roll 14 may be a shape other than the truncated pyramid shape such as a rectangular parallelepiped shape or a cylindrical shape.

FIG. 1 shows a condition where the bonder 16 as an ultrasonic sealer is retracted from the first roll 12. When the shaped sheet 6 is manufactured, the parts of the first and second sheets 2 and 4 held between a horn end 16a of the bonder 16 and the flat surfaces 12t of the seal projections 12x of the first roll 12 (see FIG. 2) are ultrasonically bonded. The bonder 16 may be a bonder that performs bonding by other than ultrasonic bonding such as a welder or bonding rolls as in the first and second conventional examples.

Next, a method of manufacturing the shaped sheet 6 by using the shaped sheet manufacturing device 10 will be described.

(1) First, the first sheet 2 is conveyed along the outer peripheral surface 12s of the rotating first roll 12. This is the first step.

(2) Then, the first and second sheets 2 and 4 pass between the first roll 12 and the second roll 14, the second sheet 4 is overlapped with the first sheet 2 so as to be held between the recessed parts 12b of the first roll 12 and the projection parts 14a of the second roll 14 and is conveyed together with the first sheet 2. This is the second step.

(3) Although detailed later, in the second step, the tension of the first sheet 2 is made smaller than that of the second sheet 4. For at least the first sheet 2 of the first and second sheets, a shapeable sheet is used. The first and second sheets 2 and 4 may be a non-stretchable non-woven fabric or may be air-through non-woven fabric.

As shown in FIG. 1, by making the second sheet 4 start to overlap with the first sheet 2 in the engagement area 13 where the recessed parts 12b and the projection parts 14a engage with each other (see FIG. 2), it is easy to adjust the tensions of the first and second sheets 2 and 4 independently of each other. The second sheet 4 may be made to start to overlap with the first sheet 2 in the engagement area 13 with the second sheet 4 being wound on the second roll 14 on the upstream side of the engagement area 13 in the conveyance direction.

However, there are cases where the shaped sheet 6 can be manufactured even if the second sheet 4 starts to overlap with the first sheet 2 on the upstream side of the engagement area 13 in the conveyance direction.

Then, the first and second sheets having passed between the first roll 12 and the second roll 14 are bonded to each other. This is the third process.

Preferably, in the third step, the first and second sheets are bonded to each other by using the bonder 16 disposed adjacent to the first roll 12 under a condition where the parts of the first sheet 2 pressed into the recessed parts 12b by the projection parts 14a remain in the recessed parts 12b. In this case, the first sheet 2 can be reliably bonded to the second sheet 4 at predetermined places around the parts pressed into the recessed parts 12b by the projection parts 14a, so that the shape of the shaped sheet 6 is stabilized.

With reference to FIGS. 3A to 3D which are explanatory views conceptually showing the shaping process, description will be further provided.

Figure 3A:
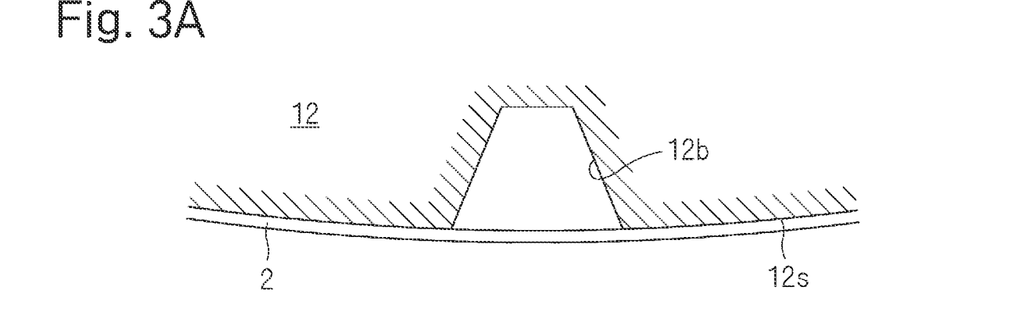
FIGS. 3A to 3D are explanatory views of a shaping process (first embodiment).
Figure 3B:
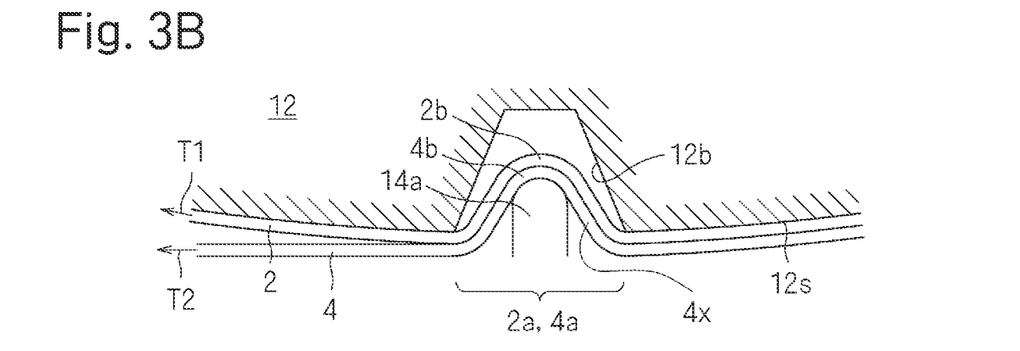

As shown in FIG. 3A, the first sheet 2 is wound on the outer peripheral surface 12s of the first roll 12, and then, as shown in FIG. 3B, the second sheet 4 is overlapped with the first sheet 2. In the engagement area 13 where the recessed parts 12b of the first roll 12 and the projection parts 14a of the second roll 14 engage with each other (see FIG. 2), parts 2a and 4a of the first and second sheets 2 and 4 facing the recessed parts 12b are pressed into the recessed parts 12b by the projection parts 14a engaging with the recessed parts 12b. Thereby, parts 2b and 4b pressed into the recessed parts 12b are formed on the first and second sheets 2 and 4.

At this time, the first and second sheets 2 and 4 deform elastically or plastically. On the downstream side in the conveyance direction of the recessed parts 12b engaging with the projection parts 14a (the right side in FIG. 3B), the first and second sheets 2 and 4 have their relative movements limited because they are overlapped with each other; on the other hand, on the upstream side in the conveyance direction of the recessed parts 12b engaging with the projection parts 14a (the left side in FIG. 3B), the first and second sheets 2 and 4 hardly or never restrain each other. For this reason, the upstream sides in the conveyance direction of the recessed parts 12b engaging with the projection parts 14a, of the first and second sheets 2 and 4 are drawn out and pressed into the recessed parts 12b.

When the first roll 12 rotates to convey the first and second sheets 2 and 4, the projection parts 14a engaging with the recessed parts 12b gradually exit from the recessed parts 12b, so that the first and second sheets 2 and 4 are gradually overlapped with each other around the recessed parts 12b.

As shown in FIGS. 1 and 3B, when the tension of the first sheet 2 immediately before being held between the recessed parts 12b and the projection parts 14a is T1 and the tension of the second sheet 4 immediately before being held between the recessed parts 12b and the projection parts 14a is T2, the tensions of the first and second sheets 2 and 4 are set so that T1<T2. For example, a known tension adjusting mechanism is provided on the upstream side of the engagement area 13 in the conveyance direction to adjust the tensions T1 and T2 so that T1<T2.

When T1=0, the parts 2b of the first sheet 2 pressed into the recessed parts 12b remain in the recessed parts 12b when passing the engagement area 13. Even when T1≠0, if T1 is small, for example, if T1≤0.05 N/mm, it is impossible to draw back the first sheet 2 to the upstream side in the conveyance direction against the friction between the first sheet 2 and the first roll 12. In this case, the parts 2b of the first sheet 2 pressed into the recessed parts 12b also remain in the recessed parts 12b.

The tension T2 of the second sheet 4 is made not more than the rupture strength of the first sheet 2, for example, 0.1 to 2 N/mm. If the tension T2 of the second sheet 4 overcomes the frictional force between the first and second sheets 2 and 4, when the projection parts 14a engaging with the recessed parts 12b exit from the recessed parts 12b thereafter, the parts 4b of the second sheet 4 pressed into the recessed parts 12b gradually exit from the recessed parts 12b.

If parts 4x of the second sheet 4 on the downstream side of the projection parts 14a in the conveyance direction are pulled to be plastically deformed and stretched when pressed into the recessed parts 12b by the projection parts 14a, the plastically deformed parts remain stretched even after the projection parts 14a exit from the recessed parts 12b. Moreover, when the second sheet 4 is simultaneously pressed into a plurality of recessed parts 12b adjoining in a direction orthogonal to or intersecting the conveyance direction and the parts between the recessed parts 12b adjoining in the direction orthogonal to or intersecting the conveyance direction are pulled to be plastically deformed and stretched, the plastically deformed parts remain stretched even after the projection parts 14a exit from the recessed parts 12b.

If the second sheet 4 is plastically deformed and stretched as described above, when passing the engagement area 13, parts 4c or the whole of the parts 4b of the second sheet 4 pressed into the recessed parts 12b (see FIG. 3B) remain in the recessed parts 12b even after the projection parts 14a exit from the recessed parts 12b, so that a slack occurs at the parts 4a covering the recessed parts 12b. The larger the tension T2 is, the more readily the second sheet 4 is plastically deformed when pressed into the recessed parts 12b. For this reason, the larger the tension T2 is, the larger the slack at the parts 4a of the second sheet 4 covering the recessed parts 12b. Even if the second sheet 4 is a non-stretchable non-woven sheet, for example, when it is heated by the first roll 12, the plastic deformation is promoted, so that a slack is formed at the parts 4a covering the recessed parts 12b.

Figure 3C:
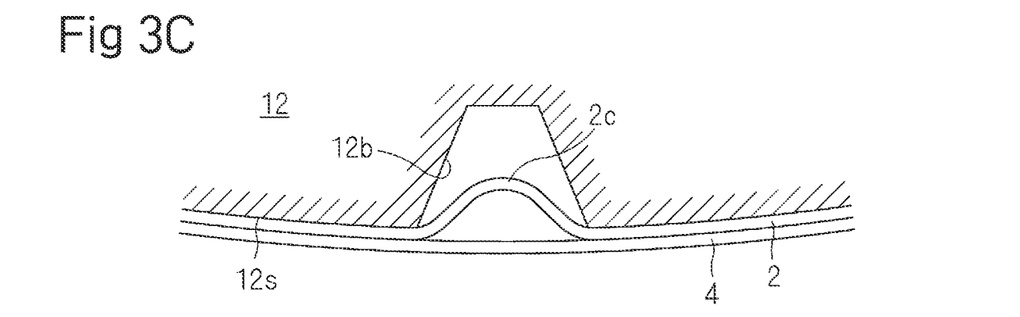
Figure 3D:
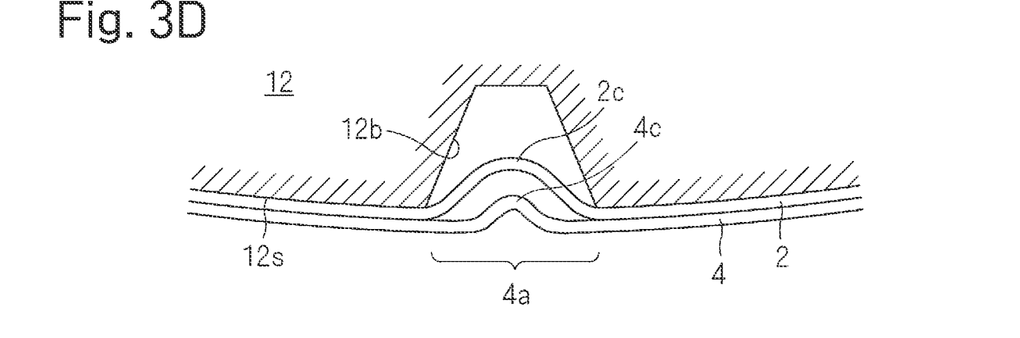

In a case where the parts 4b of the second sheet 4 pressed into the recessed parts 12b (see FIG. 3B) are completely out of the recessed parts 12b as shown in FIG. 3C when the first and second sheets 2 and 4 pass the engagement area 13, only the first sheet 2 is shaped. In a case where the parts 4c or the whole of the parts 4b of the second sheet 4 pressed into the recessed parts 12b remain in the recessed parts 12b as shown in FIG. 3D when the first and second sheets 2 and 4 pass the engagement area 13, both the first and second sheets 2 and 4 are shaped. In a case where the second sheet 4 is plastically deformed when passing the engagement area 13, both the first and second sheets 2 and 4 are shaped.

Since the parts 2b of the first sheet 2 pressed into the recessed parts 12b are covered with the second sheet 4 and are not in contact with the projection parts 14a, even if the tension T1 of the first sheet 2 is made smaller than the tension T2 of the second sheet 4, the parts 2b of the first sheet 2 pressed into the recessed parts 12b are never caught by the projection parts 14a and disengaged from the recessed parts 12b. Consequently, even if the tension T1 of the first sheet 2 is reduced, the first sheet 2 can be reliably shaped.

The second sheet 4 is shaped in a case where parts or the whole of the parts 4b pressed into the recessed parts 12b by the projection parts 14a remain in the recessed parts 12b when it passes between the first roll 12 and the second roll 14. In this case, although both the first and second sheets 2 and 4 can be simultaneously shaped, it is unnecessary to prepare a roll that shapes the second sheet 4, separately from the roll that shapes the first sheet 2. Consequently, it is possible to shape both the first and second sheets 2 and 4 without making the configuration of the shaped sheet manufacturing device 10 complex.

On the shaped sheet 6, protruding parts are formed on the first sheet 2 correspondingly to the parts 2c of the first sheet 2 pressed into the recessed parts 12b by the projection parts 14a and remain in the recessed parts 12b (see FIG. 3C).

Figure 9:
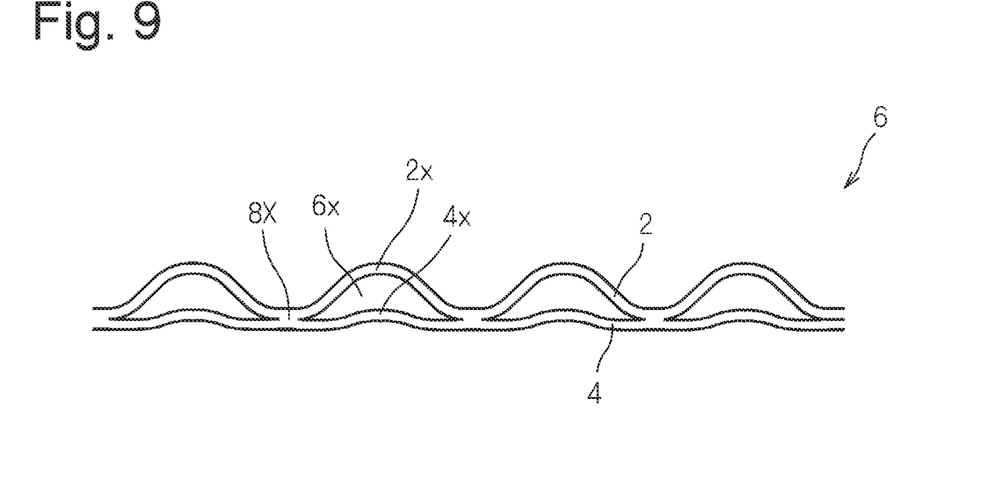
FIG. 9 is a cross-sectional view of the shaped sheet (first embodiment).

FIG. 9 is a cross-sectional view of the shaped sheet 6 manufactured by the above-described method. FIG. 9 conceptually shows an example of the cross section of the shaped sheet 6 under natural conditions where no tension is applied to the first and second sheets 2 and 4. As shown in FIG. 9, protruding parts 2x and 4x protruding to the same side are formed on the first and second sheets 2 and 4. The protruding parts 2x of the first sheet 2 are larger than the protruding parts 4x of the second sheet 4, and spaces 6x are formed between the first and second sheets 2 and 4. The first and second sheets 2 and 4 are bonded to each other at bonded parts 8x.

Next, the bonding pattern of the shaped sheet 6 will be described with reference to FIGS. 4A to 7H. In FIGS. 4A to 7H, the arrow 8 indicates the direction in which the first and second sheets 2 and 4 are conveyed (hereinafter, referred to as "flow direction"). The + sign indicates the neighborhood of the center of each protruding part of the first sheet 2 formed on the first sheet 2. The bonded parts where the first and second sheets are bonded to each other are formed correspondingly to the flat surfaces 12t of the seal projections 12x of the first roll 12 (see FIG. 2).

Figure 4A:
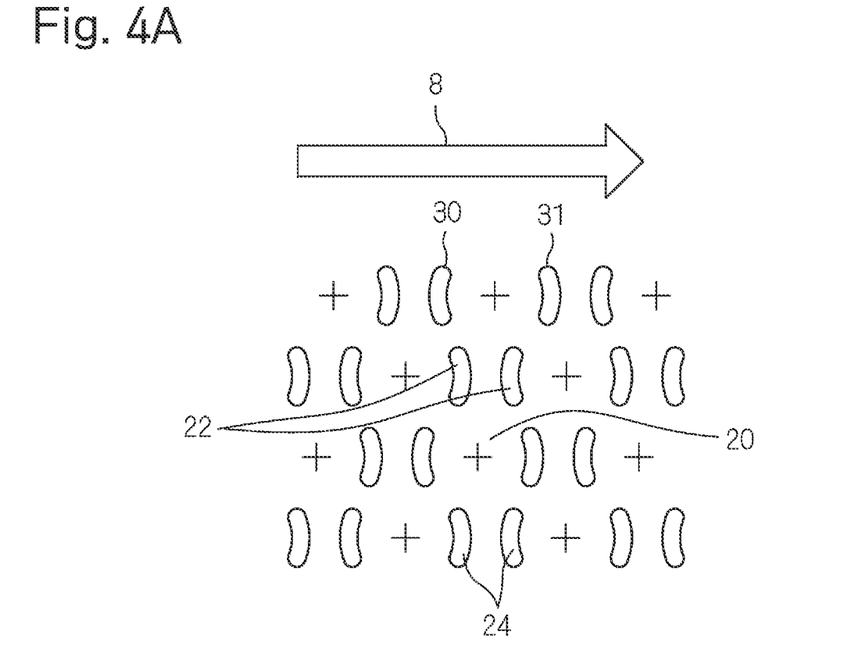
FIGS. 4A and 4B are plan views each showing a bonding pattern (first embodiment).

In the bonding pattern shown in FIG. 4A, a plurality of crescent-shaped bonded parts 30 and 31 curved in directions opposite to each other are alternately arranged at intervals in the flow direction. The protruding parts are formed between the bonded parts 30 and 31 the concave sides of which face each other. A plurality of rows in which the bonded parts 30 and 31 are arranged in the flow direction are shifted in pitch so that areas 20 where the concave sides of the bonded parts 30 and 31 face each other are held between the bonded parts 30 and 31 of pairs 22 and 24 the convex sides of which face each other in the rows on both sides.

Figure 4B:
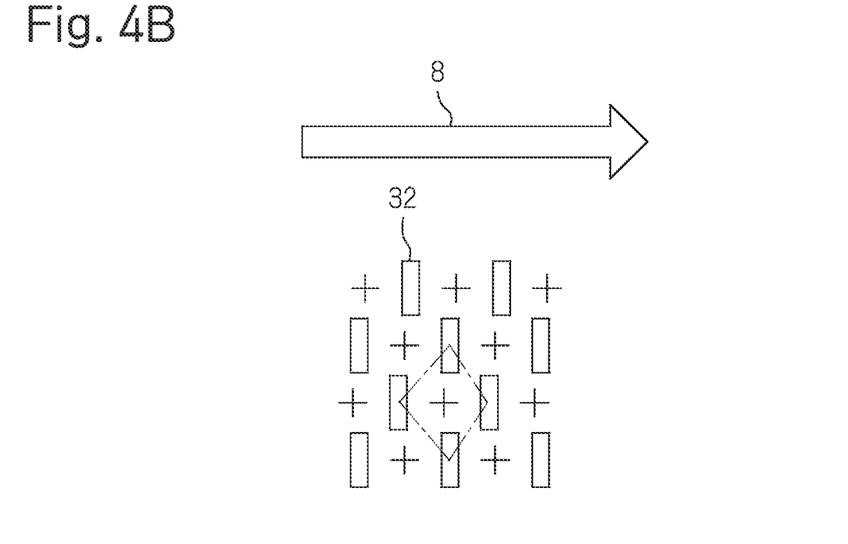

In the bonding pattern shown in FIG. 4B, rectangular bonded parts 32 are arranged at the vertices of a plurality of virtual rectangles one diagonal lines of which are parallel to the flow direction and that are arranged with no space thereamong. The protruding parts are formed inside the virtual rectangles. The chain line shows one of the virtual rectangles.

Figure 5C:
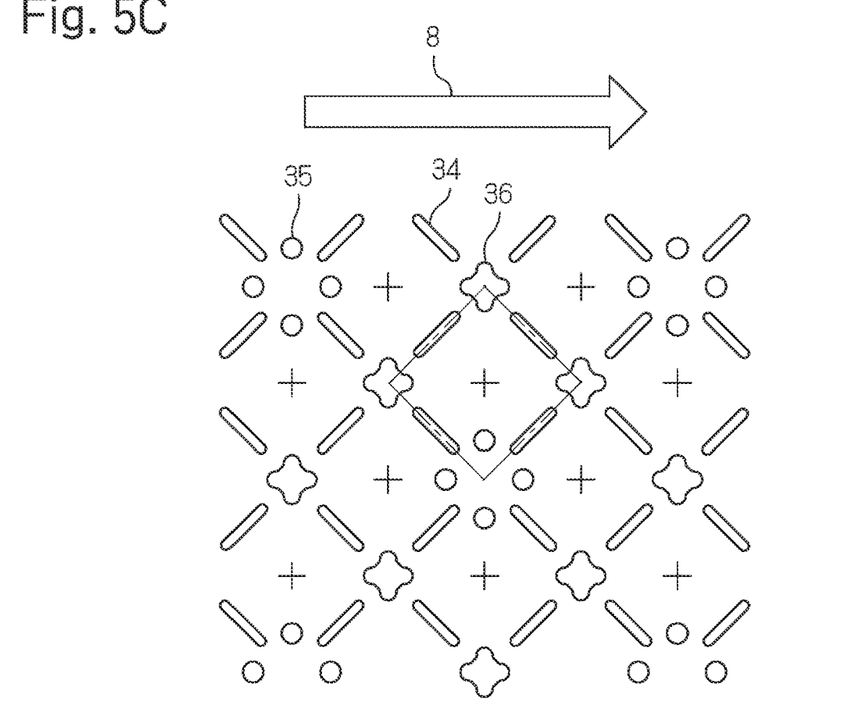
FIGS. 5C and 5D are plan views each showing a bonding pattern (first embodiment).

In the bonding pattern shown in FIG. 5C, linear bonded parts 34 are arranged on the sides of a plurality of virtual rectangles one diagonal lines of which are parallel to the flow direction and that are arranged with no space thereamong, substantially cross-shaped bonded parts 36 are arranged at three vertices of each virtual rectangle, respectively, and four circular bonded parts 35 are arranged so as to surround the remaining one vertex of each virtual rectangle. The protruding parts are formed inside the virtual rectangles. The chain line shows one of the virtual rectangles.

Figure 5D:
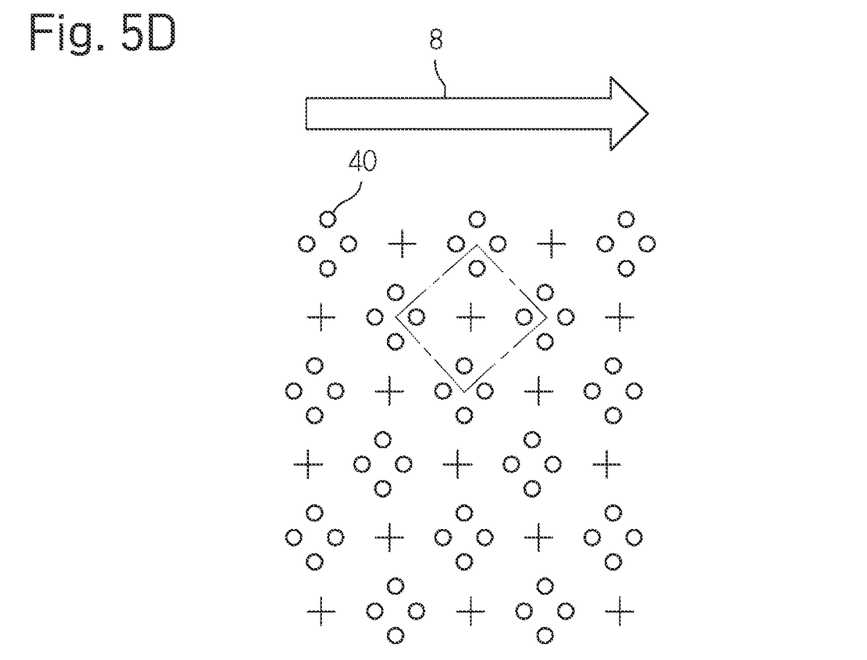

In the bonding pattern shown in FIG. 5D, four circular bonded parts 40 are arranged so as to surround the vertices of a plurality of virtual rectangles one diagonal lines of which are parallel to the flow direction and that are arranged with no space thereamong. The protruding parts are formed inside the virtual rectangles. The chain line shows one of the virtual rectangles.

Figure 6E:
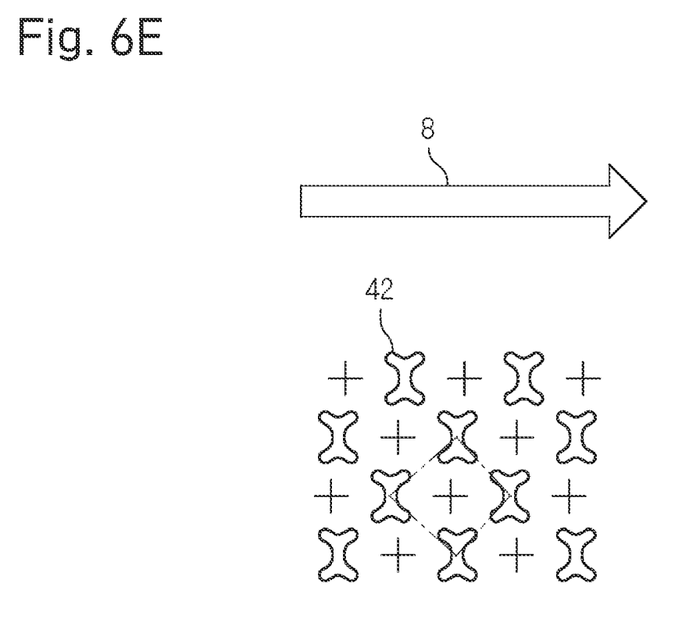
FIGS. 6E and 6F are plan views each showing a bonding pattern (first embodiment).

In the bonding pattern shown in FIG. 6E, bone-shaped bonded parts 42 are arranged at the vertices of a plurality of virtual rectangles one diagonal lines of which are parallel to the flow direction and that are arranged with no space thereamong. The protruding parts are formed inside the virtual rectangles. The chain line shows one of the virtual rectangles.

Figure 6F:
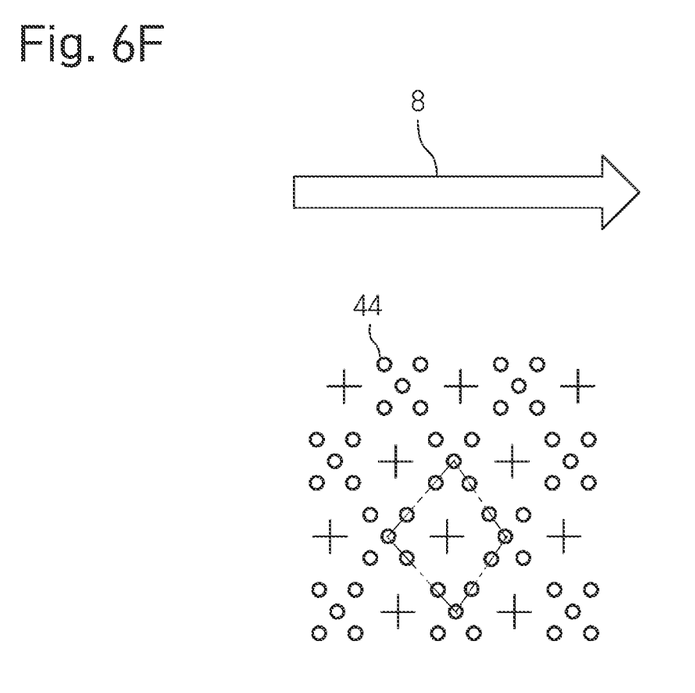

In the bonding pattern shown in FIG. 6F, five circular bonded parts 44 are arranged at and around the vertices of a plurality of virtual rectangles one diagonal lines of which are parallel to the flow direction and that are arranged with no space therebetween. The protruding parts are formed inside the virtual rectangles. The bonded parts 44 surrounding the protruding parts are arranged in a diamond shape. The chain line shows one of the virtual rectangles.

Figure 7G:
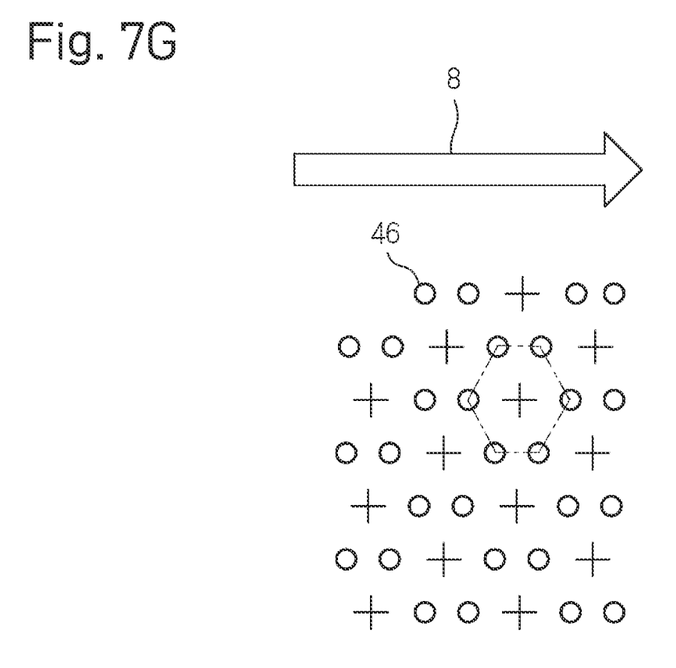
FIGS. 7G and 7H are plan views each showing a bonding pattern (first embodiment).

In the bonding pattern shown in FIG. 7G, circular bonded parts 46 are arranged at the vertices of a plurality of virtual hexagons a pair of facing sides of which are parallel to the flow direction and that are arranged with no space thereamong. The protruding parts are formed inside the virtual hexagons. The chain line shows one of the virtual hexagons.

Figure 7H:
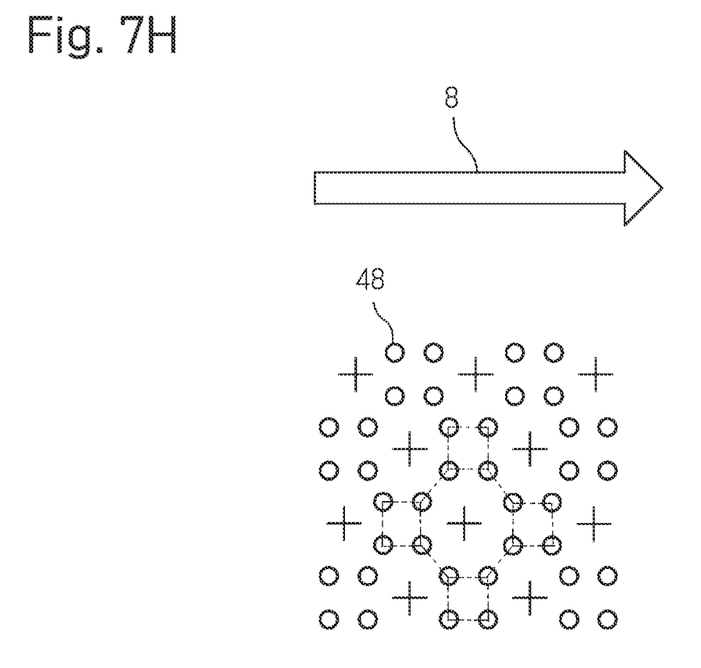

In the bonding pattern shown in FIG. 7H, circular bonded parts 48 are arranged at the vertices of a plurality of virtual octagons two pairs of facing sides of which are parallel or vertical to the flow direction. The virtual octagons are arranged with no space thereamong together with a plurality of virtual rectangles facing sides of which are parallel or vertical to the flow direction. The protruding parts are formed inside the virtual octagons. The chain lines show one of the virtual octagons and four virtual rectangles adjoining it.

Figure 8A:
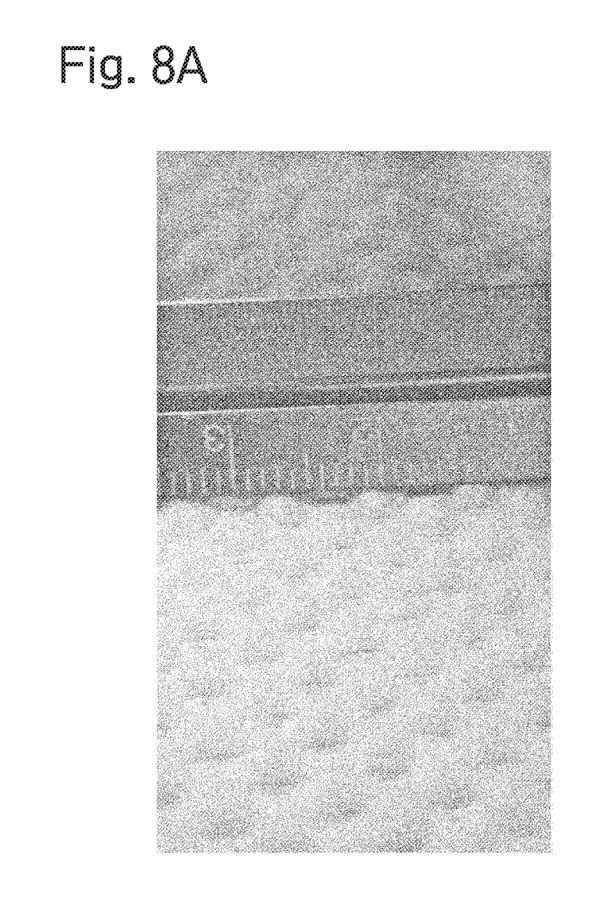
FIGS. 8A and 8B show pictures of a shaped sheet (trial product example of the first embodiment).
Figure 8B:
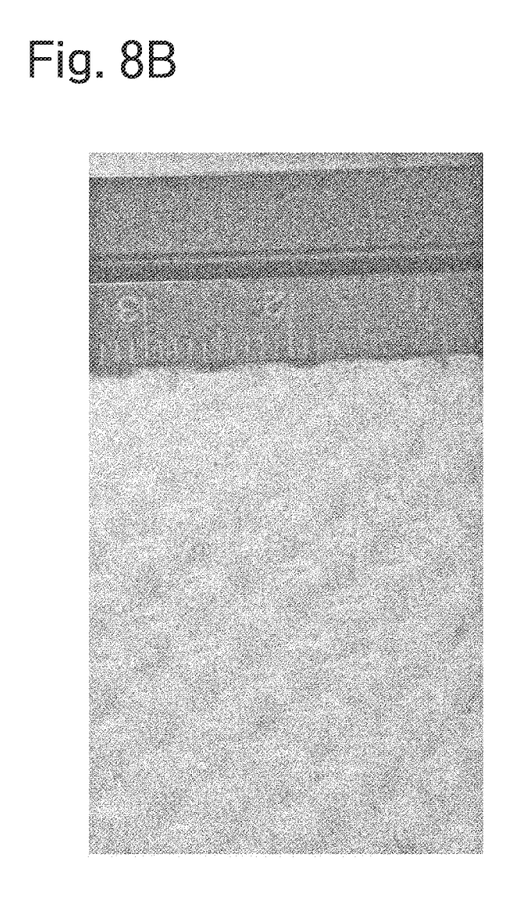

FIGS. 8A and 8B show pictures of the shaped sheet 6 manufactured by way of trial by using the shaped sheet manufacturing device 10. For the first and second sheets 2 and 4, a non-woven sheet is used that stretches in a direction vertical to the flow direction, and the first and second sheets 2 and 4 are bonded in the bonding pattern shown in FIG. 4B.

FIG. 8A shows a picture of the side of the first sheet 2. From FIG. 8A, it is apparent that protruding parts are formed on the first sheet 2. FIG. 8B shows a picture on the side of the second sheet 4. From FIG. 8B, it is apparent that the second sheet 4 is slightly recessed.

<Summary> As described above, it is possible to reliably shape the first sheet 2 even if the tension T1 of the first sheet 2 is reduced at the time of manufacturing the shaped sheet 6 in which the first and second sheets 2 and 4 are bonded to each other, and it is possible to shape both the first and second sheets 2 and 4 without making the device configuration complex.

The present invention is not limited to the above-described embodiment and may be variously modified when carried out.

EXPLANATION OF REFERENCE NUMERALS

2 First sheet
2b Pressed-in part
4 Second sheet
4b Pressed-in part
6 Shaped sheet
10 Shaped sheet manufacturing device
12 First roll
12b Recessed part
12s Outer peripheral surface
13 Engagement area
14 Second roll
14a Projection part
14s Outer peripheral surface
16 Bonder

The invention claimed is:

1. A shaped sheet manufacturing method using a shaped sheet manufacturing device comprising: a first roll having a plurality of recessed parts on an outer peripheral surface thereof; and a second roll having a plurality of projection parts on an outer peripheral surface thereof, and in which the first and second rolls are disposed adjacent to each other and rotate in synchronism and the recessed parts and the projection parts engage with each other with space therebetween, the method comprising:

a first step of conveying a first sheet which is a continuous body along the outer peripheral surface of the first roll which is rotating;

a second step of overlapping a second sheet which is a continuous body with the first sheet and conveying the second sheet together with the first sheet so that the first sheet and the second sheet pass between the first roll and the second roll and are held between the recessed parts and the projection parts; and a third step of starting, after the second step, to bond, to each other the first and second sheets having passed between the first roll and the second roll, wherein in the second step, a tension of the first sheet is made smaller than a tension of the second sheet.

2. The shaped sheet manufacturing method according to claim 1, wherein in the third step, the first and second sheets are bonded to each other by using a bonder disposed adjacent to the first roll under a condition where parts of the first sheet pressed into the recessed parts by the projection parts remain in the recessed parts.

3. The shaped sheet manufacturing method according to claim 1, wherein in the second step, the second sheet is overlapped with the first sheet so that the second sheet starts to overlap with the first sheet in an area where the recessed parts and the projection parts engage with each other with space therebetween.

4. The shaped sheet manufacturing method according to claim 1, wherein the first and second sheets are non-stretchable non-woven sheets.

5. The shaped sheet manufacturing method according to claim 2, wherein in the second step, the second sheet is overlapped with the first sheet so that the second sheet starts to overlap with the first sheet in an area where the recessed parts and the projection parts engage with each other with space therebetween.

6. The shaped sheet manufacturing method according to claim 2, wherein the first and second sheets are non-stretchable non-woven sheets.

7. The shaped sheet manufacturing method according to claim 3, wherein the first and second sheets are non-stretchable non-woven sheets.

8. The shaped sheet manufacturing method according to claim 1, wherein in the second step, on a downstream side in a conveyance direction of the recessed parts engaging with the projection parts, the first and second sheets are overlapped to limit relative movements of the first and second sheets, and on an upstream side in the conveyance direction of the recessed parts engaging with the projection parts, the first and second sheets are not restrained each other so that the first and second sheets on the upstream sides in the conveyance direction of the recessed parts engaging with the projection parts are drawn out and pressed into the recessed parts.

9. The shaped sheet manufacturing method according to claim 1, wherein in the second step, when the first and second sheets pass the first and second rollers, whole of the first sheet is pressed into the recessed part, and part of the second sheet is pressed into the recessed parts so that a slack occurs at a part covering the recessed parts.

* * * * *